(12) United States Patent
Foote

(10) Patent No.: US 7,950,289 B2
(45) Date of Patent: May 31, 2011

(54) DAMAGE SENSORS

(75) Inventor: Peter David Foote, Trellech (GB)

(73) Assignee: BAE Systems PLC, London (GB)

( * ) Notice: Subject to any disclaimer, the term of this patent is extended or adjusted under 35 U.S.C. 154(b) by 246 days.

(21) Appl. No.: 12/278,134

(22) PCT Filed: Jan. 16, 2007

(86) PCT No.: PCT/GB2007/050020
§ 371 (c)(1),
(2), (4) Date: Aug. 1, 2008

(87) PCT Pub. No.: WO2007/088395
PCT Pub. Date: Aug. 9, 2007

(65) Prior Publication Data
US 2009/0007688 A1  Jan. 8, 2009

(30) Foreign Application Priority Data

Feb. 3, 2006  (EP) ................................ 06270011
Feb. 3, 2006  (GB) ................................ 0602191.9

(51) Int. Cl.
*G01M 5/00* (2006.01)
(52) U.S. Cl. ........................................... 73/786; 73/760
(58) Field of Classification Search ............ 73/760–860
See application file for complete search history.

(56) References Cited

U.S. PATENT DOCUMENTS

| | | | |
|---|---|---|---|
| 4,565,919 A | 1/1986 | Bitter et al. | |
| 4,639,732 A * | 1/1987 | Acoraci et al. | 342/371 |
| 5,086,274 A | 2/1992 | Gobin et al. | |
| 5,195,046 A | 3/1993 | Gerardi et al. | |
| 5,440,300 A | 8/1995 | Spillman, Jr. | |
| 6,198,279 B1 * | 3/2001 | Goldfine | 324/232 |
| 6,420,867 B1 | 7/2002 | Goldfine et al. | |
| 6,709,397 B2 * | 3/2004 | Taylor | 600/459 |
| 2003/0001587 A1 | 1/2003 | Arabi | |
| 2005/0284232 A1 | 12/2005 | Rice | |
| 2006/0002815 A1 | 1/2006 | Harris et al. | |

(Continued)

FOREIGN PATENT DOCUMENTS

EP   0 895 073 B1   2/1999

(Continued)

OTHER PUBLICATIONS

Lin, Mark W., et al., "Electrical time domain reflectometry sensing cables as distributed stress/strain sensors in smart material systems," *Proceedings of SPIE*, Jun. 1997, pp. 33-41, vol. 3042, SPIE, USA.

(Continued)

*Primary Examiner* — Max Noori
(74) *Attorney, Agent, or Firm* — Buchanan Ingersoll & Rooney PC

(57) ABSTRACT

A damage sensor comprises a probe track, a sense track, and a signal generator operable to input a probe signal to the probe track. The probe track and the sense track are electromagnetically coupled by a structure on which they are provided, such that the probe signal induces, in dependence on the degree of electromagnetic coupling between the probe track and the sense track, a sensed signal in the sense track. The magnitude, phase and frequency of the sensed signal can be analysed in order to determine whether and where damage has occurred to the structure.

23 Claims, 1 Drawing Sheet

U.S. PATENT DOCUMENTS

2006/0149341 A1* 7/2006 Palti .............................. 607/63

FOREIGN PATENT DOCUMENTS

| GB | 2 350 900 A | 12/2000 |
| GB | 2 361 065 A | 10/2001 |
| JP | 10-115599 A | 5/1998 |

OTHER PUBLICATIONS

Chang, Fu-Kuo, Editor, *Structural Health Monitoring 2005*, "Proceedings of the 5th International Workshop on Structural Health Monitoring, Stanford University, Stanford CA, Sep. 12-14, 2005", pp. v-xxiii, 678-685, 756-761, DES*tech* Publications, Inc., Lancaster, PA, USA.

Form PCT/ISA/210 (International Search Report) dated Apr. 13, 2007.

Form PCT/IPEA/409 (International Preliminary Report on Patentability) dated May 13, 2008.

European Search Report dated May 19, 2006.

United Kingdom Search Report dated Jun. 29, 2006.

* cited by examiner

DAMAGE SENSORS

FIELD OF THE INVENTION

The present invention concerns improvements relating to damage sensors. More particularly, but not exclusively, the present invention relates to damage sensors for detecting the presence and occurrence of damage to a broad variety of structures such as aircraft, ships and bridges.

BACKGROUND

Structures such as aircraft airframes, ships' hulls, and bridges require regular inspections to check for damage. Inspections are currently usually performed manually according to a schedule. These scheduled inspections are precautionary, and, often, no damage is found. Such inspections are very time consuming and thus costly, since the structure will be out of use whilst the inspection is carried out. However, they are necessary since the consequences of structural failure can be catastrophic.

A number of damage or defect sensor systems are currently being developed. These systems aim to eliminate costly manual technology by enabling structures to perform 'self-inspection' using automated networks of sensors. Such self-inspection systems, if available, would allow the owners and operators of structures to benefit from lower operating costs and less frequent disruptions to use, since the structure would only be out of use if actual maintenance, to repair actual damage, were necessary. Owners and operators would also benefit from lower risk of structural failure, and therefore enhanced safety, since self-inspection systems would enable structures to be continuously monitored throughout their lives, and thus any defects in or damage to the structure would be detected sooner.

Many current sensor concepts are described in "Proceedings of the 5$^{th}$ International Workshop on Structural Health Monitoring", Stanford University, Stanford, Calif., September 2005, edited by Fu-Kuo Chang. Current techniques use powered, discrete sensors that actively probe structures using ultrasound, or use highly sensitive ultrasonic microphones that 'listen' for cracks. In currently known sensor systems a compromise must be reached between a number of conflicting factors, such as the complexity of the sensor devices, the number needed to cover a given structure, the sensitivity of the sensor devices, the size and weight of sensor installations, and the overall cost of the sensor system. For example, if it is desired to monitor a ship's bulk for damage using prior-known discrete sensors, it is necessary to use a large number of sensors in order to reliably monitor the entire hull with an appropriate degree of sensitivity. However, the cost, complexity and weight of the system increases with the number of sensors used. Furthermore, individual connections must be made to each sensor. The reliability of any electrical system decreases as the number of electrical connections required increases. The production time for the structure also increases as the number of electrical connections increases, thereby also increasing manufacture costs. For example, fitting discrete strain gauges to a modern military aircraft can add several weeks to the production time. Such sensing systems, if used for damage detection are therefore not readily scalable.

One example of a prior-known system for damage detection is that described by Mark W. Lin, Ayo O. Abatan, and Musa B Danjaji in their paper "Electrical time domain reflectometry sensing cables as distributed stress/strain sensors in smart material systems", Proceedings of SPIE Volume 3042, pages 33 to 41, June 1997. Lin et al. disclose the use of electrical time domain reflectometry (ETDR) for health monitoring applications of civil engineering structures. The ETDR sensing method disclosed by Lin et al. requires the use of a coaxial cable embedded in the structure. The cable is deformed by the stresses and strains to which the structure is exposed, and these deformations of the cable result in impedance changes which will partially reflect a signal propagating in the cable. The magnitude of the reflection is related to the degree of deformation of the cable, and so, by monitoring the cable, the stresses and strains to which the structure is exposed can be monitored. Unfortunately, it is not clear how the deformation of the cable relates to the stresses and strains to which the structure is subjected, and nor is it clear how an instantaneous measure of stresses and strains in the structure can be used to assess the level of damage to the structure.

OBJECTS AND SUMMARY OF THE INVENTION

It is an object of the invention to at least reduce or partially overcome some of the above-mentioned drawbacks. It is a further object of the invention to provide a damage sensor that is simple and quick to manufacture, cost-effective and directly sensitive to the pressure or occurrence of damage to a structure. It is an object of the present invention to provide a damage sensor that produces an output that is more simple to analyse than that of prior known damage sensors. It is also an object of the invention to provide a damage sensor with fewer electrical connections, and thus enhanced reliability and scalability, than prior known damage sensors.

In broad terms, the present invention resides in the concept of using a structure to electromagnetically couple two conducting tracks, allowing damage to the structure to be sensed by measuring the degree of electromagnetic coupling between the two tracks. This concept finds application in damage detection sensors according to embodiments of the invention, in methods of manufacture of such damage sensor, and in methods of sensing damage to a structure. Damage sensors according to embodiments of the invention are directly sensitive to the characteristics of the structure being monitored, and can be fabricated rapidly and cheaply by using, for example, direct-write techniques to print tracks on to a structure.

In accordance with a first aspect of the present invention, there is provided a damage sensor for sensing damage to a structure, the damage sensor comprising a probe track, a sense track, and a signal generator operable to input a probe signal to the probe track, the probe track and the sense track being electromagnetically coupled by the structure such that the probe signal induces, in dependence on the degree of electromagnetic coupling between the probe track and the sense track, a sensed signal in the sense track. The term "electromagnetically coupled", when used herein, is intended to be construed broadly to include, for example, coupling by electromagnetic waves, such as optical signals, radio-frequency signals or terahertz-frequency signals; or coupling by purely electric signals through conduction and capacitive effects. Because the sensed signal is related to the degree of electromagnetic coupling between the probe track and the sense track, and this electromagnetic coupling is due to the structure, the damage sensor is directly sensitive to the electromagnetic properties of the structure. Therefore, any damage that changes the electromagnetic properties of the structure is visible in the sensed signal. This direct sensitivity is advantageous in that it allows simple analysis techniques (such as comparing a sensed signal to a reference signal, measured when the structure was known to be undamaged) to be reliably used.

The damage sensor is thus sensitive to, for example, mechanical damage that causes physical disruption to the structure, thereby changing its electrical and electromagnetic properties; and to chemical damage, due, for example, to chemical influences, such as the ingress of moisture or other foreign materials, that degrade the integrity of the structural material and thereby change the electromagnetic properties of the structure. Damage such as, for example, the presence of cracks, delamination in laminate structures, infusion of foreign matter, or the presence of corrosion will also be visible in the sensed signal.

The damage sensor is also scaleable to larger structures: by extending the probe and sense tracks, a larger area can be monitored by the sensor. Advantageously, the larger area of the structure can be monitored without increasing the number of electrical connections. It may be possible to monitor even very large structures whilst using only two electrical connections. This leads to enhanced reliability of the damage sensor. Furthermore, extending the probe and sense tracks does not introduce any significant weight penalty, and the damage sensor can therefore readily be applied to structures such as aircraft, where there exists a need to control weight.

The probe track and the sense track may be integral with the structure. Preferably, the probe track and the sense track are provided on the surface of the structure. In this way, a damage sensor according to the present invention can easily be added to an existing structure. Of course, it may be necessary to paint over the damage sensor, or apply other layers above the tracks, as will be understood by those skilled in the art.

The probe track and the sense track may be substantially parallel, such that the degree of electromagnetic coupling of the probe track and the sense track is approximately uniform along their length. Analysis of the resulting signal is thus made simpler, since variations in electromagnetic coupling along the length of the wing can be attributed immediately to structural effects, rather than to variations in track separation.

The probe signal may be chirped. Chirped signals have rapidly changing frequency so that the frequency of the probe signal will vary with position on the probe track. Advantageously, this allows the position of any damage indicated by the sensed signal to be deduced from the frequency of the portion of the sensed signal at which damage is apparent. Optionally, the frequency of the probe signal is swept at a rate in the range 0.1 GHz per second to 10 GHz per second. The probe signal may be swept at a rate of 3 GHz per second.

Alternatively, the probe signal may be pulsed. Pulses are of sufficiently short duration for the position of any indicated damage to be deduced from the time of arrival of the damage-indicating portion of the sensed signal. The pulse duration therefore determines the accuracy to which damage-indicating portions of the signal can be correlated with spatial locations. Pulse duration may be selected to suit specific applications. Optionally, the pulse duration is in the range 0.1 to 10 picoseconds. Advantageously, such a pulse duration provides millimetric spatial location accuracy.

Optionally, the probe track and the sense track cover substantially the whole of the structure. It is to be noted that structure, herein, is to be understood to mean the structure of an aircraft, ship, or other vehicle; or a building or bridge; or a component panel of such a structure. When the probe track and sense track cover substantially the whole of the structure, such that the area to which the sensor is sensitive is representative at the whole structure, the damage sensor provides a monitoring system for the whole structure.

A frequency selector may be provided in operable association with the probe track and the sense track; the frequency selector, the probe track and the sense track in combination forming a sensing element, which sensing element is one of a plurality of interconnected similar sensing elements; and wherein a first sensing element of the plurality of sensing elements, which first sensing element comprises a first frequency selector, is operable independently of the other sensing elements at a predetermined frequency selected by the first frequency selector. Advantageously, the position of any sensed damage can be deduced, to within the area covered by a given sensing element, from the frequency at which damage is indicated. This provides a simple system for sensing the position of any damage to the structure. Conveniently, the plurality of sensing elements covers substantially the whole of the structure. Preferably, the plurality of sensing elements comprises a first set of sensing elements aligned substantially orthogonally to a second set of sensing elements. Advantageously, the position of damage can then be sensed within two dimensions.

The probe track and the sense track may be printed onto the surface of the structure. This allows a cost-effective and rapid fabrication technique to be used, that can readily be applied to existing structures.

According to a second aspect of the invention, there is provided a method for sensing damage to a structure, the method comprising the steps of:
 (a) providing a probe signal in a probe track, which probe track is electromagnetically coupled to a sense track by the structure;
 (b) measuring a sensed signal in the sense track, the sensed signal being induced, in dependence on the degree of electromagnetic coupling between a probe track and the sense track, in the sense track; and
 (c) comparing the sensed signal to a reference signal recorded earlier to determine whether the structure has been damaged between the step of recording the reference signal and the step of measuring the sensed signal.

Conveniently, the method is simpler than prior known damage sensing methods, since no assumptions must be made about the coupling of the sensor to the structure. Preferably, the step of providing a probe signal comprises the step of providing a varying frequency probe signal such that the frequency of the probe signal is dependent on its position along the probe track, and such that the magnitude of the sensed signal at a first frequency is dependent on the degree of electromagnetic coupling between the probe track and the sense track at a first position related to the first frequency. This allows the position of any damage to the structure to be deduced.

According to a third aspect of the invention, there is provided a method of manufacturing a damage sensor comprising the step of direct-writing a probe track and a sense track onto a structure. Direct-writing is a known technique of adding functionality to surfaces, for example by rapidly printing, painting or depositing materials onto surfaces in precisely controlled patterns. Typically, directly-written features could be conductive tracks or complex multi-layered patterns made from a variety of materials. For example, when manufacturing a damage sensor in accordance with embodiments of the invention, the probe and sense tracks may be simple conducting tracks, or, if the structure is metallic, there may be an additional layer of insulating material interleaved between the surface of the structure and the conducting track. Both the insulating layer and the conducting track could be added to the surface using direct-write technology. Such a method is cost-effective, rapid, and readily applicable to existing structures using existing technology. Such a method can also be readily incorporated into existing manufacturing processes. Optionally, the method additionally comprises the step of direct-writing a frequency selector onto a structure. Conveniently, the frequency selector comprises a capacitor and an inductor.

It is to be understood that the invention extends to a vehicle comprising a damage sensor as described above. The vehicle may be an aircraft, ship, submarine, or land vehicle.

DETAILED DESCRIPTION

Figure 1:
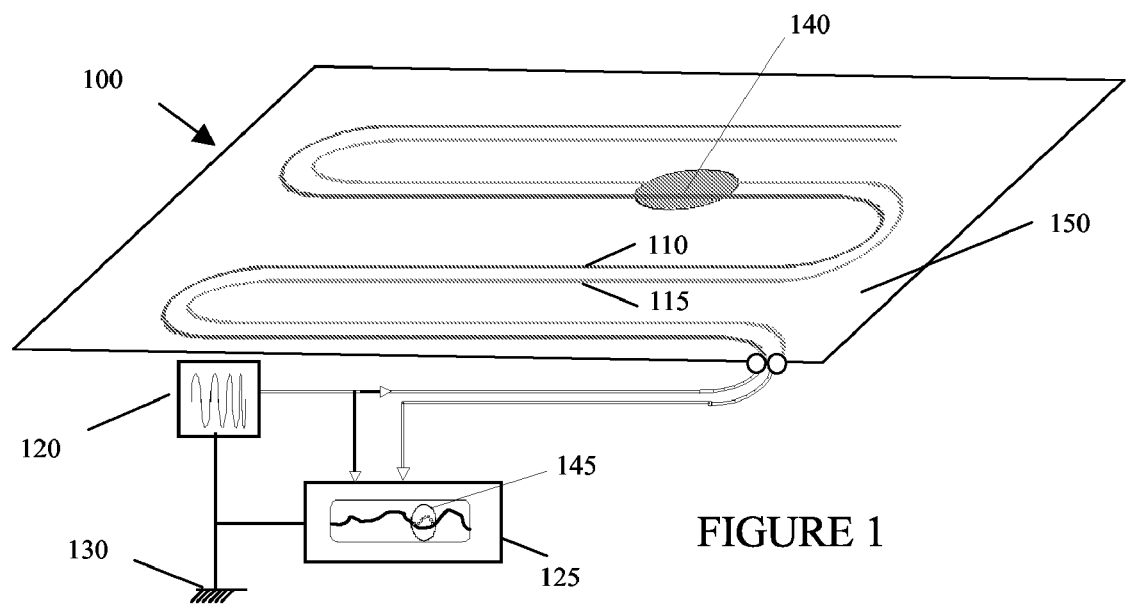
FIG. 1 is a schematic view of a damage sensor according to a first embodiment of the invention.

FIG. 1 schematically shows a damage sensor 100 according to a first embodiment of the invention. Damage sensor 100 comprises a probe track 110 and a sense track 115. The probe track 110 and sense track 115 are printed directly onto the structure 150 to be monitored. Structure 150 could be an aircraft airframe, or a ship's hull. The probe track 110 and sense track 115 are electromagnetically coupled by the structure 150. Uniform electromagnetic coupling between the probe track 110 and the sensor track 115 is achieved by arranging tracks 110, 115 on the surface of structure 150 in a parallel configuration such that they are separated by a gap of uniform width along their length. If it is desired to monitor the whole of structure 150, the tracks 110, 115 should be further arranged to extend over substantially the whole of the structure. The term "substantially the whole of the structure", will be understood by those skilled in the art to mean at least a representative portion of the structure, such that a reliable measure of the damage to the structure can be obtained. For example, the tracks may be arranged in a serpentine configuration that extends over a large part of structure 150, as is illustrated in FIG. 1.

In addition to probe track 110 and sense track 115, damage sensor 100 also comprises a signal generator 120, and signal analyser 125. Signal generator 120 is operable to input a probe signal to the probe track 110. Signal analyser 125 is connected to the sense track 115, and also receives a reference signal, similar to the probe signal, from the signal generator. Both the signal generator and the signal analyser are connected to ground at 130.

In operation of damage sensor 100, therefore, a probe signal is input from the signal generator 120 to the probe track 110. Since probe track 110 is electromagnetically coupled to sense track 115 by structure 150, the probe signal induces a sensed signal in sense track 115. The magnitude, phase and frequency of the sensed signal will depend on the degree of electromagnetic coupling between the probe track 110 and the sense track 115, and in particular on the electrical impedance of the material of the structure between tracks 110 and 115. The probe signal is a chirped signal, a high frequency sinusoid that is rapidly and linearly swept in frequencies. For example, given a signal travelling at 70% of the speed of light, a sweep rate of 3 GHz per second would produce a signal frequency change of 1 Hz for every 7 cm of track length. Therefore, a receiver of notional 1 Hz bandwidth would be able to resolve signals to within 7 cm anywhere along the track. In this way, at any given instant time, the frequency of a signal at a particular point on the probe track 110 is related to the position of that particular point along the probe track. The frequency of the sensed signal is thus also related to the position at which it is induced, as well as the electrical impedance of the material of the structure between tracks 110 and 115. An impedance map of the structure can therefore be drawn up after appropriate analysis of the sensed signal.

Measuring a first impedance map, when the structure 150 is known to be in an undamaged state, provides a characteristic map against which future sensed impedance maps can be compared. Any damage to the structure will affect the electrical impedance of the structure local to the damaged area. A crack, for example, will cause a local increase in electrical impedance. Such a change in the impedance of the structure will be immediately apparent on comparison of the sensed impedance map to the characteristic map. For example, referring to FIG. 1, an area of damage 140 affects the impedance of the material in area 140, and particularly the impedance of the material between the probe track 110 and sense track 115 in region 140. The change in impedance causes a change in the sensed impedance map as compared to the characteristic map, at a frequency related to the position of the area 140 along the tracks 110, 115. This is indicated schematically at 145, and it is immediately clear from comparison of the characteristic map to the sensed impedance map that damage has accrued.

It is noted that the required separation between the probe track 110 and the sense track 115 will vary depending on the electrical characteristics of the structure 150. Both metallic and insulating structures can be monitored using damage sensor 100, but the width of the gap and the characteristics of the tracks 110, 115 must be tailored to suit the requirements of the application. For most applications, it is expected that the width of the gap would be of the order of a few millimeters. Its precise value is determined after thoroughly characterising the material and geometric characteristics of the structure on which the sensor is to be installed. Such a characterisation is performed prior to the installation of the sensor.

A second embodiment of the invention will now be described, which uses the same apparatus as described above with reference to FIG. 1. In accordance with the second embodiment, the probe signal is a short pulse instead of the varying frequency sinusoid described above. As the pulse travels along the probe track, it induces a sensed signal in the sense track. The signal analyser receives a sensed signal that is a waveform with duration equal to the time taken for the probe signal pulse to travel the length of the probe track. The magnitude of the sensed signal will depend on the degree of electromagnetic coupling between the probe track 110 and the sense track 115, and in particular on the electrical impedance of the material of the structure between the tracks 110 and 115. For a pulse of sufficiently short duration, the local impedance at a first point along the probe track 110 and sense track 115 can be calculated from the magnitude of the waveform at a time corresponding to the time taken for the pulse to travel to the first point. The pulse will travel along the probe track at a speed that is a significant fraction of the speed of light, and so to resolve distances along the track of the order of centimeters, the duration of the pulse must be of the order of picoseconds. For example, the pulse duration may be in the range 0.1 to 10 picoseconds. Very fast electronic equipment is therefore required in order for methods according to the second embodiment to the performed in a signal generator capable of generating picosecond pulse, and a signal analyser capable of responding accurately to signals varying on the picoseond timescale.

The method of the first embodiment can be termed "frequency domain reflectrometry" in order to distinguish it from the "time domain reflectometry" of the second embodiment. Frequency domain reflectometry is preferred for the present invention because, whilst in terms of analysis it may be more complex, it does not require as fast electronic equipment as time domain reflectometry. This makes frequency domain reflectometry a more cost effective option.

Figure 2:
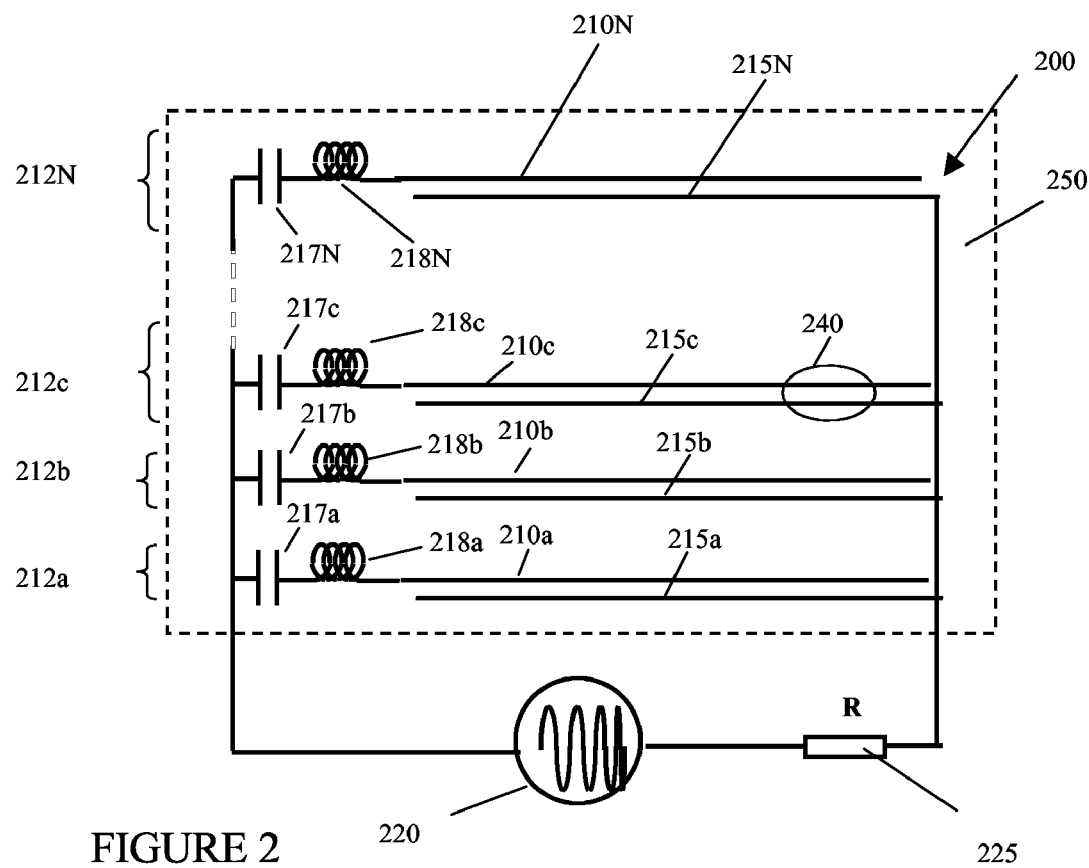
FIG. 2 is a schematic view of a damage sensor according to a third embodiment of the invention.

FIG. 2 shows a damage sensor 200 according to a third embodiment of the invention. Damage sensor 200 comprises a number of sensing elements 212a-N. Each sensing element comprises a frequency selector, a probe track 210 and a sense track 215. For example, sensing element 212a comprises a frequency selector, probe track 210a and sense track 215a. The sensing elements are interconnected in parallel, and connected to a signal generator 220 and a signal analyser 225. The frequency selectors comprise inductors 218 and capacitors 217—for example, the frequency selector for sensing element 212b comprises capacitor 217b and inductor 218b. In combination, the inductor and capacitor in each frequency selector form a resonant circuit. Each sensing element is chosen to operate at a distinct frequency, by trimming capacitors 217 and inductors 218 to tune the resonant frequency of each frequency selector. Each sensing element 212 thus operates at the resonant frequency of its frequency selector. For example, an inductor of 1 nH inductance in combination with a capacitor of 1 nF capacitance will result in a circuit having a resonant frequency of 1 GHz. The sharpness of the resonance, or Q-factor, will depend on local resistance of the track. The resonant frequencies of the frequency selectors are adjusted such that resonant peaks of different frequency selectors do not overlap.

The interconnected sensing elements 212 are printed onto the surface of a structure 250, which structure is to be monitored for damage, using direct-write techniques. The elements 212 are arranged such that the probe track and sense track in each sensing element are electromagnetically coupled by the structure, and such that the individual sensing elements 212 are not significantly electromagnetically coupled by the structure. Thus the probe tracks must be significantly closer to their respective sense tracks than to their neighbouring sensing elements. The probe track and sense track in each sensing element are arranged on the structure 250 in a parallel configuration. Preferably, the gaps separating the probe and sense tracks within each sensing element are uniform, such that a uniform electromagnetic coupling exists between each probe and sense track. As described above with reference to FIG. 1, the required size of the gaps will vary in dependence on the material characteristics of the structure, and the size of the gap and quality of the tracks can be tailored to suit a given structure.

In operation of the third embodiment, a sinusoidal signal is input into probe tracks 210 through the frequency selectors. The frequency of the sinusoidal signal, which forms the probe signal, is scanned through the range of frequency defined by the resonant frequencies of the frequency selectors. When the structure 250 is undamaged, the scan provides a characteristic response to which later scans can be compared. If an area of damage is present at a later point, for example an area of damage 240 extending over sensing element 212, there will be a change in the response as compared to the earlier obtained characteristic response. This change will be visible at the resonant frequency of sensing element 212c, thereby allowing the location of the damage to be determined to be along sensing element 212c. Since the resonant frequencies of the frequency selectors are chosen such that they do not overlap, The response at other frequencies is unchanged from the characteristic response, since damaged area 240 does not extend to sensing elements other than sensing element 212c.

Additional sensitivity to the location of the damage can be achieved by placing a second set of sensing elements on top of sensing elements 212 but oriented perpendicular to sensing elements 212. Such an additional set of sensing elements would allow the position of a damaged area to be determined in two dimensions.

Damage sensors according to embodiments of the invention can be fabricated by a simple direct-write process, in which the component parts of the damage sensor are printed directly onto the structure. Probe and sense tracks, and frequency selectors, can be printed onto a structure using ink jet technology, or other known direct-write technologies. Conventional computer printer heads are available to print features as small as a few tens of microns, so that it is possible to direct-write damage sensors according to the present invention onto structures using existing, conventional technologies. Conducting inks can be printed directly onto insulating structures. In the case of metallic, conducting structures it may be necessary to first print a dielectric ink onto the structure so as to avoid shorting of the probe track to the sense track. Single or multi-layer deposition is possible, and the components of the damage sensor can be printed either in single or multi-step processes.

Once the sensing elements, including probe and sense tracks, and any frequency selectors, have been printed onto the surface of the structure, connections can be made to the signal generator and signal analyser. These are the only connections that need to be made to complete fabrication of the damage sensor. The fabrication method is thus cost effective and simple, since a very small number of electrical connections need to be made (in comparison to prior art damage sensors), and the direct-write process is simpler, quicker and cheaper than, for example, wire-bonding techniques used prior to the invention. In addition, the small number of electrical connections results in enhanced reliability for the damage sensor.

Various equivalents and modifications to the above-described embodiments are possible without departing from the scope of the invention, as will be obvious to those skilled in the art. For example, whilst in the above it has been described to use a parallel configuration of probe and sense tracks, it would be possible for any configuration to be used, provided that the probe and sense tracks are sufficiently electromagnetically coupled by the structure for damage to be readily apparent on comparing characteristic and sensed impedance maps to be used.

In addition, whilst it has been described in the above to use a frequency selector comprising an inductor and a capacitor, it would also be possible to use a frequency selector comprising a radio-frequency filter having periodic features. As will be readily understood by those skilled in the art, the components of, for example, the frequency selector and the probe and sense tracks will be determined by the frequency range of the probe signal. Different frequency ranges may be appropriate for structures having different material characteristics. For example, if optical frequencies were to be used, the tracks would be optical waveguides or optical fibres, and the frequency selectors would comprise optical filters, or other optical frequency selective components. Optical frequencies may be appropriate for materials such as polycarbonates, or some resin systems, such as glass-fibre reinforced plastic (GRP) systems. However, the degree of coupling between two optical waveguides, even if treated to leak radiation at certain points, is expected be small—such that the appropriate separation between the probe and sense tracks is expected to be of the order of a few microns, rather than of the order of a few millimeters.

Furthermore, whilst in the above it has been described to use a pulsed or chirped probe signal, it will be understood that any time-varying signals could also be used to provide the probe signal. Any time-varying probe signal will induce a similarly time-varying signal in the sense wire. Provided that both probe and sense signals can be synchronously digitised with sufficient temporal resolution, cross-correlations of the two signals may be used to produce a characteristic map of coupling between probe and sense tracks to which later measurements can be compared, in the same manner as described above. For example, a sample rate of 500 MHz would be able to resolve distances along the probe and sense tracks to approximately 0.5 m.

The above embodiments are to be understood as illustrative examples of the invention. Further embodiments are envisaged. It is to be understood that any feature described in relation to any one embodiment may be used alone, or in combination with other features described, and may also be used in combination with one or more features of any of the other embodiments, or any combination of any of the other embodiments. Furthermore, equivalent and modifications not described above may also be employed without departing from the scope of the invention, which is defined in the accompanying claims.

The invention claimed is:

1. A damage sensor for sensing damage to a structure, the damage sensor comprising:
    a probe track;
    a sense track;
    a signal generator operable to input a time-varying probe signal to the probe track, the probe track and the sense track being electromagnetically coupled by the structure such that the probe signal induces, in dependence on the degree of electromagnetic coupling between the probe track and the sense track, a sensed signal in the sense track; and
    a signal analyzer operable to receive and measure the sensed signal from which sensed signal an impedance map indicative of both damage and the location of the damage to the structure is derivable.

2. A damage sensor as claimed in claim 1 wherein the probe track and the sense track are integral with the structure.

3. A damage sensor as claimed in claim 1 wherein the probe track and the sense track are provided on the surface of the structure.

4. A damage sensor as claimed in claim 1 wherein the probe track and the sense track are substantially parallel.

5. A damage sensor as claimed in claim 1 wherein the probe signal is chirped.

6. A damage sensor as claimed in claim 5 wherein the frequency of the probe signal is swept at a rate in the range 0.1 GHz to 10 GHz.

7. A damage sensor as claimed in claim 6 wherein the probe signal is swept at a rate of 3 GHz.

8. A damage sensor as claimed in claim 1 wherein the probe signal is pulsed.

9. A damage sensor as claimed in claim 8 wherein the probe signal duration is in the range 0.1 to 10 picoseconds.

10. A damage sensor as claimed in claim 1 wherein the probe track and the sense track cover substantially the whole of the structure.

11. A damage sensor as claimed in claim 1, wherein a frequency selector is provided in operable association with the probe track and the sense track; the frequency selector, the probe track and the sense track in combination forming a sensing element, which sensing element is one of a plurality of interconnected similar sensing elements; and wherein a first sensing element of the plurality of sensing elements, which first sensing element comprises a first frequency selector, is operable independently of the other sensing elements at a predetermined frequency selected by the first frequency selector.

12. A damage sensor as claimed in claim 11 wherein the plurality of sensing elements covers substantially the whole of the structure.

13. A damage sensor as claimed in claim 11 wherein the plurality of sensing elements comprises a first set of sensing elements aligned substantially orthogonally to a second set of sensing elements.

14. A damage sensor as claimed in claim 1 wherein the probe track and the sense track are printed onto the surface of the structure.

15. A method for sensing and locating damage to a structure, the method comprising the steps of:
    (a) providing a time-varying probe signal in a probe track, which probe track is electromagnetically coupled to a sense track by the structure;
    (b) measuring a sensed signal in the sense track, the sensed signal being induced, in dependence on the degree of electromagnetic coupling between a probe track and the sense track, in the sense track;
    (c) comparing the probe signal and the sensed signal to derive an impedance map of the structure;
    (d) comparing the impedance map to a characteristic map recorded earlier to determine whether the structure has been damaged between the recording of the characteristic map and the measuring of the impedance map; and
    (e) determining the location of the damage from comparison of the impedance map with the characteristic map.

16. A method as claimed in claim 15, wherein the probe track and the sense track are integral with the structure.

17. A method as claimed in claim 15 wherein the probe track and the sense track are provided on the surface of the structure.

18. A method as claimed in claim 15, wherein the step of providing a probe signal comprises the step of providing a varying frequency probe signal such that the frequency of the probe signal is dependent on its position along the probe track, and such that the magnitude of the sensed signal at a first frequency is dependent on the degree of electromagnetic coupling between the probe track and the sense track at a first position related to the first frequency.

19. A method of manufacturing a damage sensor for sensing and locating damage to a structure, the damage sensor comprising:
    a probe track;
    a sense track;
    a signal generator operable to input a time-varying probe signal to the probe track, the probe track and the sense track being electromagnetically coupled by the structure such that the probe signal induces, in dependence on the degree of electromagnetic coupling between the probe track and the sense track, a sensed signal in the sense track; and
    a signal analyzer operable to receive and measure the sensed signal, from which sensed signal an impedance map indicative of damage and the location of the damage to the structure is derivable;
    the method comprising the step of direct-writing a probe track and a sense track onto the structure.

20. A method as claimed in claim 19, further comprising the step of direct-writing a frequency selector onto the structure.

21. A method as claimed in claim 20, wherein the frequency selector comprises a capacitor and an inductor.

22. A vehicle comprising a damage sensor for sensing damage to a structure, the damage sensor comprising:
- a probe track;
- a sense track;
- a signal generator operable to input a time-varying probe signal to the probe track, the probe track and the sense track being electromagnetically coupled by the structure such that the probe signal induces, in dependence on the degree of electromagnetic coupling between the probe track and the sense track, a sensed signal in the sense track; and
- a signal analyzer operable to receive and measure the sensed signal, from which sensed signal an impedance map indicative of both damage and the location of the damage to the structure is derivable.

23. A damage sensor as claimed in claim 1, wherein the signal analyser is operable to:
- a) receive the input time-varying probe signal from the signal generator; and
- b) compare the probe signal and the sensed signal to derive the impedance map of the structure.

* * * * *